(12) United States Patent
Wilson et al.

(10) Patent No.: US 8,247,231 B2
(45) Date of Patent: Aug. 21, 2012

(54) METHODS AND COMPOSITIONS FOR PRODUCING ANTIGENIC RESPONSES

(76) Inventors: Constance N. Wilson, Raleigh, NC (US); Paul Borron, Durham, NC (US)

( * ) Notice: Subject to any disclaimer, the term of this patent is extended or adjusted under 35 U.S.C. 154(b) by 0 days.

(21) Appl. No.: 10/903,933

(22) Filed: Jul. 30, 2004

(65) Prior Publication Data
US 2005/0075308 A1    Apr. 7, 2005

Related U.S. Application Data

(60) Provisional application No. 60/491,510, filed on Jul. 31, 2003.

(51) Int. Cl.
*C12N 5/00* (2006.01)
*C12N 5/02* (2006.01)
*C12N 15/00* (2006.01)

(52) U.S. Cl. ........................................ 435/455; 435/377

(58) Field of Classification Search .................. None
See application file for complete search history.

(56) References Cited

U.S. PATENT DOCUMENTS

| | | | |
|---|---|---|---|
| 3,920,811 A | 11/1975 | Lund | |
| 6,159,701 A | 12/2000 | Neely | |
| 6,680,052 B1 * | 1/2004 | Neely | 424/93.7 |
| 2002/0160415 A1 | 10/2002 | Neely | |
| 2003/0129678 A1 | 7/2003 | Neely | |
| 2005/0220799 A1 | 10/2005 | Sitkovsky et al. | |

FOREIGN PATENT DOCUMENTS

| | | |
|---|---|---|
| WO | WO 9819541 A1 * | 5/1998 |
| WO | WO 02/095391 | 11/2002 |
| WO | WO 03/050241 | 6/2003 |

OTHER PUBLICATIONS

Piemonti et al., 1999, Glucocorticoids increase the endocytic ativity of human dendritic cells. Int. Immunol. vol. 11: 1519-1526.*
Wang et al., 2005, Thalidomide-dexamethasone as primary therapy for advance multiple myeloma. Am. J. Hem. vol. 79:194-197.*
Ren et al., 1994, Characterization of the Human A1 adenosine receptor gene. J. Biol. Chem. vol. 4: 3104-3110.*
Tuting et al., 1998, Autologous human MDC genetically modified to express melanoma antigens elicit primary cytotoxic T cell responses in ivtor. J. Immunol. vol. 160: 1139-1147.*
Panther et al., 2001, Expression and function of adenosine receptors in human dendritic cells. FASEB J., vol. 15: 1963-1970.*
Zhou et al., 2005, Identification of HCC-22-5 tumor associated antigen and antibody resposne in patients. Clinica Chimica Acta, in press./.*
Tsimberidou, 2002, Blood, vol. 100: 4351-4357.*
Engelbrecht et al., 2003, Endocrinology, vol. 144: 412-422.*
Robeva et al., 1996, Biochem. Pharm. vol. 51: 545-555.*
Chaperot et al., 2000, Leukemia, vol. 14: 1667-1677.*
Sun et al., 2005, J. Clin. Invest. vol. 115: 35-43.*
Helene et al., 2000, Human Gene Therapy, vol. 11: 1259-1267.*
Burke et al., 2002, J. Leuk Biol. vol. 72: 417-428.*
Hendersone t al., 1996, Canc. Res. VOI 56: 3763-3770.*
Panther, E., et al., "Expression and Function of Adenosine Receptors in Human Dendritic Cells," *The FASEB Journal*, pp. 1963-1970, vol. 15, 2001.
Schnurr, M., et al., Role of Adenosine Receptors in Regulating Chemotaxis and Cytokine Production of Plasmacytoid Dendritic Cells, *Blood*, pp. 1391-1397, vol. 103(4), 2004.
Cytotoxic T cell, Wikipedia, http://en.wikipedia.org/wiki/Cytotoxic_T_cell, Oct. 7, 2010.
Transfection, Wikipedia, http://en.wikipedia.org/wiki/Transfection, Oct. 14, 2010.
Electroporation, Wikipedia, http://en.wikipedia.org/wiki/Electroporation, Oct. 14, 2010.
Lipofection, Wikipedia, http://en.wikipedia.org/wiki/Lipofection, Oct. 14, 2010.
Fotheringham, J.A., et al., "Activation of Adenosine Receptors Inhibits Tumor Necrosis Factor-$\alpha$ Release by Decreasing TNF- $\alpha$mRNA stability and P38 activity," *European Journal of Pharmacology*, 2004, pp. 87-95, vol. 497.
La Sala, A., et al., "Dendritic Cells Exposed to Extracellular Adenosine Triphosphate Acquire the Migratory Properties of Mature Cells and Show a Reduced Capacity to Attract Type 1 T Lymphocytes," *Blood*, 2002, pp. 1715-1722, vol. 99(5).
Panther, E., et al., "Adenosine Affects Expression of Membrane Molecules, Cytokine and Chemokine Release, and the T-cell Stimulatory Capacity of Human Dendritic Cells," *Blood*, 2003, pp. 3985-3990, vol. 101(10).

* cited by examiner

*Primary Examiner* — Amy Juedes
(74) *Attorney, Agent, or Firm* — James G. Passé; Passé Intellectual Property, LLC

(57) ABSTRACT

The present invention relates to methods of producing an antigenic response in which an antigen is contacted to an antigen-presenting cell, wherein the improvement comprises contacting the antigen-presenting cell with an $A_1$ adenosine receptor activating agent in an amount sufficient to increase the antigenic response of the antigen-presenting cell to the antigen. The present invention further provides methods, compositions, combination therapies, imaging techniques, and diagnostic kits that may improve the diagnosis, prognosis, and/or survival of cancer patients, pathogen-infected patients, and infectious or non-infectious immune-deficient patients.

16 Claims, No Drawings

METHODS AND COMPOSITIONS FOR PRODUCING ANTIGENIC RESPONSES

RELATED APPLICATION

This application claims the benefit of U.S. Provisional Patent Application Ser. No. 60/491,510 filed Jul. 31, 2003, entitled Methods and Compositions for Producing Antigenic Responses, the disclosure of which is incorporated by reference herein in its entirety.

FIELD OF THE INVENTION

The present invention relates to methods of producing antigenic responses, increasing cytotoxic responses, enhancing $A_1$ adenosine receptor signaling, treating conditions described herein, and additionally relates to compositions for achieving the same.

BACKGROUND OF THE INVENTION

Antigen Presenting Cells (APCs) play a role in the complex response of the immune system. For example, pathogen recognition receptors are present on APCs and serve to recognize a foreign antigen to the human body, bind to that antigen and present that antigen to lymphocytes to induce antigen-specific lymphocytes to produce protective immunity. Pathogen recognition receptors are essential for APCs to present antigens to lymphocytes to induce them to produce adaptive immunity—(a) humoral immunity in the form of production of antibodies and (b) cell-mediated immunity, e.g. the production of cytotoxic T lymphocytes, activated macrophages, activated natural killer cells, cytokines, and the like.

$A_1$ adenosine receptors are pathogen recognition receptors. It has been reported that lipopolysaccharide binds to $A_1$ adenosine receptors. Wilson, C N and Batra V K, J Endotoxin Research 8:263-271, (2002). Moreover, $A_1$ adenosine receptors are present on human dendritic cells, monocytes, macrophages, lymphocytes and peripheral blood mononuclear cells. Panther, E, et al FASEB J 15: 1963, (2001); Salmon J E, J Immunol 151:2775, (1993); Marone G, Int J Clin Lab Res 22:235, (1992); Marone G, Int Arch Allergy Appl Immunol 77:259, 1985; Mayne M, Ann Neurol 45:633, 1999). Additionally, treatment of immature human dendritic cells in vitro with adenosine does alter expression of cell surface markers considered important for dendritic cell function. Panther E, Blood 101:3985, (2003). Panther et al. have published research that suggests adenosine "may control proinflammatory activities of DC's and regulate their accumulation at target sites" (Panther et al. (2001)), but also published a study concluding that the $A_2$ adenosine receptor is responsible for the phenotypic changes in dendritic cell function. Panther et al. Blood 101(10): 3985-3990 (2003).

In spite of the foregoing, a potential relationship between immune deficiency and deficient $A_1$ adenosine receptor function has not been previously examined outside the area of multiple sclerosis where it has been reported that $A_1$ adenosine receptor expression is reduced in monocytes/macrophages in blood and brains of patients with multiple sclerosis. Johnston J B, Ann Neurol 49:650 (2001); Mayne M, Ann Neurol 45:633 (1999).

SUMMARY OF THE INVENTION

The present invention provides methods and compositions that may improve the prognosis of cancer patients, pathogen infected patients, infectious or non-infectious immune deficient patients, and patients with autoimmune diseases, graft-versus host disease, or rejection of a transplanted organ.

An aspect of the present invention relates to a method of producing an antigenic response comprising contacting an antigen-presenting cell with an $A_1$ adenosine receptor activating agent in an amount sufficient to increase the antigenic response of the antigen-presenting cell to the antigen.

Another aspect of the present invention relates to a method of producing an antigenic response comprising transfecting or electroporating an antigen-presenting cell with a nucleotide sequence encoding an $A_1$ adenosine receptor in a manner sufficient to increase the antigenic response of the antigen-presenting cell to the antigen.

A further aspect of the present invention relates to a method of increasing a cytotoxic response induced by a cytotoxic cell comprising contacting the cytotoxic cell with an $A_1$ adenosine receptor agonist in an amount sufficient to increase the cytotoxic response of the cytotoxic cell.

An additional aspect of the present invention relates to method of enhancing $A_1$ adenosine receptor signaling in an antigen-presenting cell, comprising administering an activating agent to the antigen-presenting cell in an amount sufficient to enhance $A_1$ adenosine receptor signaling in the antigen-presenting cell.

A further aspect of the present invention relates to methods of preventing desensitization of $A_1$ adenosine receptor responses, comprising (a) administering to an antigen-presenting cell a desensitizing agent in an amount sufficient to prevent desensitization of $A_1$ adenosine receptor responses in said antigen-presenting cell, or (b) transfecting or electroporating said antigen-presenting cell with a nucleotide sequence encoding a protein capable of preventing desensitization of $A_1$ adenosine receptor responses.

Another aspect of the present invention relates to compositions and pharmaceutical compositions comprising: (i) an antigen, and (ii) an activating agent.

A further aspect of the present invention relates to the use of compositions as described above comprising at least the antigen and the activating agent for the preparation of a medicament for the treatment of conditions described herein.

An additional aspect of the present invention relates to methods of immunizing a mammal against an antigen comprising the composition described above comprising at least the antigen and the activating agent.

A further aspect of the present invention relates to methods of treating conditions as described herein.

Another aspect of the present invention relates to methods of imaging antigen-presenting cells in vivo in a subject, comprising (a) obtaining a sample of antigen-presenting cells from a subject; (b) labelling said antigen-presenting cells with a radiolabelled $A_1$ adenosine receptor ligand, nucleotide sequence encoding the $A_1$ adenosine receptor; and then (c) administering said labelled antigen-presenting cells to the subject in an amount effective to provide a radioimage.

An additional aspect of the present invention relates to methods of imaging antigen-presenting cells in vivo in a subject, comprising (a) obtaining a sample of antigen-presenting cells from a subject; (b) labelling said antigen-presenting cells with a radiolabelled antigen; (c) contacting the antigen-presenting cells with the radiolabelled antigen and an $A_1$ adenosine receptor activating agent in an amount sufficient to increase the antigenic response of said antigen-presenting cells to said antigen; and then (d) administering said labelled antigen-presenting cells to the subject in an amount effective to provide a radioimage.

A further aspect of the present invention relates to methods imaging antigen-presenting cells in vivo in a subject, comprising (a) obtaining a sample of antigen-presenting cells from a subject; and (b) contacting the antigen-presenting cell with a biosensor that recognizes a specific target on the antigen-presenting cell, with the proviso that the biosensor is not a radiolabelled biosensor.

An additional aspect of the present invention relates to methods of determining a subject's potential responsiveness to treatment for conditions associated with $A_1$ adenosine receptor deficiency comprising determining $A_1$ adenosine receptor expression, affinity, or function on antigen-presenting cells.

Another aspect of the present invention relates to combination therapies and treatments for treatment of conditions associated with an $A_1$ adenosine receptor deficiency including diseases disclosed herein.

A further aspect of the present invention relates to diagnostic kits for determining a subject's potential responsiveness to treatment for conditions associated with $A_1$ adenosine receptor deficiency comprising at least one reagent for determining $A_1$ adenosine receptor expression, affinity, or function on antigen-presenting cells of the subject, and printed instructions for assessing the subject's responsiveness to treatment for conditions associated with $A_1$ adenosine receptor deficiency, packaged together in a container.

DETAILED DESCRIPTION OF THE INVENTION

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs.

All U.S. patent applications to Neely and U.S. patents to Neely cited herein are incorporated by reference in their entireties.

The practice of the present invention will employ, unless otherwise indicated, conventional methods of virology, chemistry, biochemistry, recombinant technology, immunology and pharmacology, within the skill of the art. Such techniques are explained fully in the literature. See, e.g., Virology, 3rd Edition, vol. I & II (B. N. Fields and D. M. Knipe, eds., 1996); Remington's Pharmaceutical Sciences, 18th Edition (Easton, Pa.: Mack Publishing Company, 1990); Methods In Enzymology (S. Colowick and N. Kaplan, eds., Academic Press, Inc.); Handbook of Experimental Immunology, Vols. I-IV (D. M. Weir and C. C. Blackwell, eds., 1986, Blackwell Scientific Publications); Sambrook et al., Molecular Cloning: A Laboratory Manual (2nd ed. 1989); and DNA Cloning: A Practical Approach, vol. I & II (D. Glover, ed.).

As used herein, the term "antigen" refers to any agent that elicits an antigenic response wherein the antigenic response refers to the initiation of a reaction responsive to the presence of a substance. The antigenic response may be an immune response.

As used herein, the term "immune response" refers to the activities of the immune system, including activation and proliferation of specific cytotoxic T-cells, after contact with an antigen. Immunity relates to the body's ability to resist organisms or toxins that can damage tissues and organs. Adaptive or acquired immunity refers to defense mechanisms that are induced or stimulated by exposure to foreign substances, are specific for distinct macromolecules and increase in magnitude and defensive capabilities with each successive exposure to a particular macromolecule. There are basically two types of acquired immunity: (1) humoral immunity or B cell immunity and (2) cell-mediated immunity or T cell immunity. Components of innate immunity include the different defense mechanisms employed to protect a host against microbes include physical barriers, phagocytic cells in the blood and tissues, natural killer cells and various blood-borne molecules. These mechanisms can repel, destroy or hold in check many classes of microbes. Some of these defense mechanisms (a) are present prior to exposure to infectious microbes or foreign macromolecules, (b) do not discriminate among most foreign substances, and (c) frequently cannot be sufficiently enhanced by such exposure.

As used herein, the term "effector cell" refers to cells capable of eliciting a response to an antigen in the immune response pathway.

As used herein, the term "immunomodulator" refers to an agent that is able to modulate an immune response as defined herein.

As used herein, the term "cytotoxic" refers to cellular dysfunction, deterioration and/or cell death.

As used herein, the term "$A_1$ adenosine receptor signaling" refers to responses mediated through $A_1$ adenosine receptors. These responses include, but are not limited to, cytotoxic responses, tumoricidal responses, production of biological response modifiers, internal processing of the antigen, internal expression of certain proteins that play a role in the immune response, e.g. major histocompatibility complex (MHC) class I or II or human leukocyte antigen (HLA) protein expression or the expression of other proteins that play a role in signaling pathways that participate in immune responses, e.g. NF-κβ, or human genes for IL-6, IL-1β, TNF-α, and other responses that facilitate an effective immune response.

As used herein, the term "activating agent" refers to any agent, method, or condition capable of activating antigen-presenting cells. As used herein, "activating" may include, and is not limited to, stimulating $A_1$ adenosine receptors, increasing $A_1$ adenosine receptor expression, increasing $A_1$ adenosine receptor coupling to signal transduction pathways, e.g. coupling to guanine nucleotide binding proteins, and interference with desensitization of $A_1$ adenosine receptor responses. As used herein, "activated" cells are those that illicit an antigenic response as described herein. Activating agents include, but are not limited to, $A_1$ adenosine receptor agonists. Activating agents may also include transfection or electroporation with nucleotide sequences encoding the $A_1$ adenosine receptor, administration of cisplatin, dexamethasone, daunorubicin, doxorubicin, mitoxantrone, carbamazepine, adenosine receptor antagonists, allosteric enhancers, protein kinase inhibitors, and conditions such as ischemia and reperfusion or ischemia alone. Activating agents may be administered or carried out in the presence or absence of the antigen.

As used herein, the term "biological response modifier" refers to any agent, method, or condition capable of affecting a biological, chemical and/or physiological response including, but not limited to, stimulating the body's response to infection or disease. Non-limiting examples of biological response modifiers include metabolic products of metabolism of arachidonic acid, including prostaglandins, thromboxane and leukotrienes; products of lipid peroxidation and lipid mediators; platelet activating factor, reactive oxygen species; cytokines, including IL-6 and TNF-alpha; chemokine; ATP; ADP; adenosine; proteases; elastases; selecting; adhesion molecules; integrins; signal transduction proteins, including G proteins; protein kinases and NF-κβ.

As used herein, the term "contacting" a cell with a substance means (a) providing the substance to the environment of the cell (e.g., solution, in vitro culture medium, anatomic fluid or tissue) or (b) applying or providing the substance directly to the surface of the cell, in either case so that the substance comes in contact with the surface of the cell in a manner allowing for biological interactions between the cell and the substance. The contacting step may be carried out in vitro or in vivo. The contacting step may include the in vitro use of transfection, pulsing or electroporation of the cells with the substance, or the combination of these methods to increase the antigenic response of the cell. See e.g., Kim K-W, et al. *Cancer Immunol Immunother* 53:315-322, 2004. The contacting step may further include the use of magnetic beads to provide sufficient contact between the substance and cell.

As used herein, the term "vaccine" is an antigenic preparation, including, e.g., a protein, a peptide, or a polysaccharide, administered to stimulate the recipient's humoral and cellular immune systems to one or more of the antigens present in the vaccine preparation. "Vaccination" or "immunization" is the process of administering a vaccine and stimulating an immune response to an antigen.

As used herein, the word "concurrently" means sufficiently close in time to produce a combined effect (that is, concurrently may be simultaneously, or it may be two or more events occurring within a short time period before or after each other).

As used herein, the administration of two or more compounds "in combination" means that the two compounds are administered closely enough in time that the presence of one alters the biological effects of the other. The two compounds may be administered simultaneously (i.e., concurrently) or sequentially. Additionally, simultaneous administration may be carried out by mixing the compounds prior to administration, or by administering the compounds at the same point in time but at different anatomic sites or using different routes of administration.

The phrases "concurrent administration," "administration in combination," "simultaneous administration" or "administered simultaneously" as used herein, interchangeably mean that the compounds are administered at the same point in time or immediately following one another. In the latter case, the two compounds are administered at times sufficiently close that the results observed are indistinguishable from those achieved when the compounds are administered at the same point in time.

Moreover, methods described herein can be performed "in combination" or "simultaneously" with other methods described herein or with known methods or treatments of interest to achieve the desired result.

Suitable subjects to be treated according to the present invention include both avian and mammalian subjects, preferably mammalian. Mammals according to the present invention include but are not limited to canine, felines, bovines, caprines, equines, ovines, porcines, rodents (e.g. rats and mice), lagomorphs, primates, and the like, and encompass mammals in utero. Humans are preferred. Human subjects of both genders and at any stage of development (i.e., neonate, infant, juvenile, adolescent, adult) can be treated according to the present invention.

Illustrative avians according to the present invention include chickens, ducks, turkeys, geese, quail, pheasant, ratites (e.g., ostrich) and domesticated birds (e.g., parrots and canaries), and include birds in ovo. Chickens and turkeys are preferred.

Any mammalian subject in need of being treated according to the present invention is suitable. The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes.

In view of the foregoing, embodiments according to the present invention relate to a method of producing an antigenic response in which an antigen is contacted to an antigen-presenting cell, the improvement comprising contacting the antigen-presenting cell with an $A_1$ adenosine receptor agonist in an amount sufficient to increase the antigenic response of said antigen-presenting cell to the antigen.

The antigenic response may be an immune response such as an adaptive immune response or an innate immune response. The immune response may be eliciting antibody formation without development of immunity or immunity may be developed. The immune response may relate to the production of higher antibody titres, increase in antibody affinity, or generation of cytotoxic cells. The immune response may also be a phenotypic or genotypic increase in responsiveness to an antigen wherein the cell internalizes and processes the antigen presented to an effector cell that in turn produces responses including, but not limited to, a cytotoxic response, tumoricidal response, tolerogenic response, or production of biological response modifiers. The immune response may include, presentation of an antigen, including but not limited to a self-antigen, by an immature dendritic cell to a T cell to induce a state of tolerance in T cells. After acquiring tolerance to an antigen, tolerized T cells may not respond effectively against the antigen when presented with the antigen. Spiotto M T, et al, Curr Opin Immunol 15:725-730, 2003. Additionally, following exposure to the antigen, the antigen presenting cell may be induced to produce a direct immune response independent of an effector cell.

The antigen may be any agent that elicits an immune response. The antigen may be a peptide, protein, lipid, carbohydrate, nucleic acid, a mucin, a proteoglycan and combinations and derivatives, i.e., modifications thereof, such as a mucoprotein, lipoprotein, glycoprotein, or glycolipid. Modifications of the antigen may include changes in epitopes of the antigen which produces an antigenic response. The antigen may be a live microorganism or a non-living compound or composition. Antigens may be derived from any of several known viruses, bacteria, parasites and fungi, whether active or inactive. The antigen may be derived from a cell or a cell component thereof, such as a cell surface molecule. The antigen may be derived from a cancer, including from the cancer cells, cell surface molecules, or any other molecule on the cancer cell or tumor cell lysates. The antigen may be an antibody-inducing determinant. The antigen may further comprise the following non-limiting components: interleukin-1 (IL-1) including IL-1α, IL-1β, interleukin-2 (IL-2), interleukin-3 (IL-3), interleukin-4 (IL-4), interleukin-5 (IL-5), interleukin-6 (IL-6), interleukin-7 (IL-7), interleukin-8

(IL-8), interleukin-9 (IL-9), interleukin-10 (IL-10), interleukin-11 (IL-11), interleukin-12 (IL-12), interleukin-13 (IL-13), interleukin-15 (IL-15), interleukin-16 (IL-16), interleukin-17 (IL-17), prostaglandins, thromboxane, leukotrienes, platelet activating factor (PAF), lipid A, phospholipase A2, endotoxins, staphylococcal enterotoxin B, Type I Interferon, Type II Interferon, tumor necrosis factor-alpha (TNF-α), transforming growth factor-beta (TGF-β), lymphokines, lymphotoxin migration inhibition factor, granulocyte-macrophage colony-stimulating factor (CSF), monocyte-macrophage CSF, granulocyte CSF, vascular epithelial growth factor (VEGF), angiogenin, transforming growth factor (TGF-α), heat shock proteins (HSPs), carbohydrate moieties of blood groups, Rh factors, fibroblast growth factor (FGF), eosinophil (EOS) cationic protein, EOS granule proteins, RANTES (regulated on activation, normal T cell expressed and secreted), nucleotides, nucleosides, DNA, RNA, mRNA, MART, MAGE, BAGE, mutant p53, tyrosinase, AZT, angiostatin, endostatin, tumor, cancer, viral infections, bacterial infections, fungal infections, atypical bacterial infections, parasitic infections, protozoal infections, self-antigens, alloantigens, transplant antigens, graft antigens, oncofetal antigens, tumor associated mucins, tumor-derived peptides, tumor cell lysates, toxins, dead cells, necrotic cells, lipopolysaccharide (LPS), exotoxin, enterotoxin, 1,3 beta glucan, peptidoglycan, lipoteichoic acid, mannose, flagellin, pilin, glycolipids, zymosan, cytokines, chemokines, immune complexes, haptens, alcohol, drugs, monocyte chemoattractant protein (MCP), MCP-1, MCP-3, MCP-4, MIF, HMGB1, MIP-1α, MIP-1β, MIP-3α, MIP-5/human cc cytokine-2 (HCC2), CD40 ligand (CD 40L), TNF-related activation induced cytokine (TRANCE), Flt 3 ligand (FL), c-kit, C5a, complement, stem cell factor (SCF), hepatocyte growth factor (HGF), macrophage-derived chemokines (MDC), stromal cell derived factor-1α (SDF-1α), prions, bovine spongiform encephalomyelitis protein (BSE), prostate specific antigen (PSA), prostate alkaline phosphatase (PAP), amyloid precursor protein (APP), amyloid beta (Abeta), tau, xenoantigens, superantigens, ovalbumin, ragweed, house dust mite, plant pollens and other plant molecules, insect toxins, $A_1$ adenosine receptors, $P_{2X}$ purinoceptors, B cell receptors, T cell receptors, antibodies, including autoantibodies, IgE, chemicals, and combinations thereof.

Examples of $A_1$ adenosine receptor agonists include, but are not limited to, adenosine; cyclohexyladenosine; various $N^6$-substituted $A_1$ adenosine agonists including but not limited to $N^6$ cyclopentyladenosine, $N^6$R-phenylisopropyladenosine, 2-chloro $N^6$ cyclopentyl adenosine (CCPA), $N^6$ (p-sulfophenyl)alkyl and $N^6$ sulfoalkyl derivatives of adenosine (such as $N^6$-(p-sulfophenyl)adenosine; 1-deaza analogues of adenosine including but not limited to $N^6$ cyclopentyl 1-2-chloro-1-deaza adenosine (1-deaza-2-Cl-CPA); $N^6$ cycloaklyladenosines; $N^6$ bicycloalkyladenosines; ribose modified adenosine receptor analogues including but not limited to 3'-deoxy-R-PIA. See, e.g., Conti, *Naunyn-Schmiedeberg's Arch. Pharmacol.* 348:108 (1993); Trivedi, *J. Med. Chem.* 32:8 (1989); Jacobsen, *J. Med. Chem.* 35:4143 (1992); Thedford, *Expl. Cell. Biol.* 57:53 (1989); Trewyn, *Exp. Pharmacol.* 28:607 (1979); Fleysher, *J. Amer. Chem. Soc.* (August 1968); Fleysher, *J. Amer. Chem. Soc.* (November 1969)); cycloalkyladenosines (see e.g., Moos, *J. Med. Chem.* 28:1383 (1985)); analogs of R-PIA, CHA, and CPA (see, e.g., Cristalli, *J. Med. Chem.* 31:1179 (1988)). Van der Wenden, *J. Med. Chem.* 38:4000 (1995); Jacobson, *PJM Med. Res. Rev.* 12:423 (1992); Daly, *J. Med. Chem.* 25:197 (1982). The binding of these $A_1$ adenosine receptor agonists to $A_1$ adenosine receptors and their activation may be enhanced by an allosteric enhancer such as P(2-amino-4,5-dimethyl 1-3-thienyl)-[3-trifluoromethyl phenyl]methadone. Additional $A_1$ adenosine receptor agonists are known in the art (see, e.g., Abstracts from Purines '96, *Drug Dev. Res.*, March 1996: Knutsen et al. (p. 111); Franchetti et al. (p. 127); Di Francesco et al. (p. 127); van der Wenden et al. (p. 128); Kirkpatrick et al. (p. 128); van Schaick et al. (p. 128)). Optimal dosing and administration schedules may be determined using routine methods known to those in the art.

Antigen-presenting cells are well known to those of ordinary skill in the art. Antigen-presenting cells may be obtained from any source, such as peripheral blood mononuclear cells, peripheral blood monocytes, circulating stem cells, stem cells or precursor cells derived from bone marrow, peripheral blood, or cord blood, or antigen-presenting cells may be found in tissue parenchyma, generated in vitro, obtained from a commercial source or cloned. Antigen-presenting cells include, but are not limited to, monocytes, macrophages, dendritic cells, Langerhans cells, lymphocytes, hematopoetic stem cells, peripheral blood stem cells, peripheral blood mononuclear cells, B cells, veiled cells, interdigitating and follicular cells, splenocytes, thymocytes, microglia, Kupffer cells, endothelial cells, fibroblasts, eosinophils, and any cell displaying HLA-peptide complexes on its cell surface. In some embodiments, the antigen-presenting cells express at least one $A_1$ adenosine receptor.

According to other embodiments of the present invention, the method of producing an antigenic response as described above may further comprise priming the antigen-presenting cell by contacting the antigen-presenting cell with a priming agent in an amount sufficient to prime the antigen-presenting cell, and activating the antigen-presenting cell by contacting the antigen-presenting cell with an activating agent in an amount sufficient to induce the antigen-presenting cells to mediate an increase in immune response to an antigen.

The cells may be treated or "primed" to enhance $A_1$ adenosine receptor activity. Cells may be primed prior to activation. For example, antigen-presenting cells may be primed using any priming agent known in the art including, but not limited to, PMA (see, e.g., Leaver, *FEMS Microbiol. Immunol.* 47:293 (1989); White, *J. Biol. Chem.* 259:8605 (1984)); lipopolysaccharide (LPS) (see, e.g., Glaser, *J. Biol. Chem* 265:8659 (1990); Pace, *J. Immunol.* 126:1863 (1981); Alexander, *Nature New Biol.* 232:76 (1971)); platelet activating factor (PAF) (see, e.g., Stewart, *Immunology* 78:152 (1993); Salzer, *J. Clin. Invest.* 85:1135 (1990)); tumor necrosis factor alpha (TNF$_\alpha$) or thrombin (see, e.g., Stewart, *Immunology* 78:152 (1993)); f-met-leu-phe (FMLP) (see e.g., Stewart, *Immunology* 78:152 (1993)); zymosan (Rankin, *J. Clin. Invest.* 86:1556 (1990); macrophage stimulating factors including granulocyte macrophage colony stimulating factor (GM-CSF); ionomycin (for example in 1 µM amounts); calcium ionophore (such as A 23187, for example in 0.1-10 µM amounts); gamma interferon (IFNγ, for example in 1-150 units/ml amounts) Flebbe, *J. Immunol.* 145:1505 (1990); supernatants of tumor cells (Hamilton and Adams, *Immunology Today* 8:151 (1987); Marvin, *J. Surg. Res.* 63:248 (1996)); or bacterial products from gram positive organisms. See, e.g., Bacterial Endotoxin Lipopolysaccharides, Morrison and Ryan (Eds.) CRC Press, Boca Raton, Fla., 1992; Hamilton and Adams, *Immunology Today* 8:151 (1987); Loppnow, *Methods Enzymol.* 236:3 (1994). Preferred priming conditions for the type of cell to be activated may be determined using routine methods known to those in the art. For example, resident tissue macrophages may be primed with PMA in vivo, in the tumor or in tissues surrounding the tumor to be treated, then exposed to an $A_1$ adenosine receptor agonist in order to activate the macrophages.

Priming of cells to increase $A_1$ adenosine receptor activation may further include subjecting the cells to hypoxia and reoxygenation, for example, by placing cells (for example, macrophages) in a cell chamber and subjecting them to low oxygen tension (e.g., 0-12% oxygen) for a suitable time (e.g., from about 5 minutes to about 48 hours, more preferably from about 2 hours to about 4 hours), prior to treatment with a priming agent as discussed above. See Lum, *Circ. Res.* 70:991 (1992); Ogawa, *Am. J. Physiol* 262:C546 (1992); Milhoan, *Am. J. Physiol.* 263:H956 (1992); Arya, *J. Surg. Res.* 59:13 (1995). Optimal hypoxia and reoxygenation conditions may be determined by routine experimentation as would be apparent to one skilled in the art. Such treatment of the cells is designed to increase $A_1$ adenosine receptor activity. Increased $A_1$ adenosine receptor activity may be due, for example, to an increase in the number of receptors, an increase in G-protein ($G_i$ protein responsible for coupling of $A_1$ adenosine receptors to signal transduction pathways), or an increase in enzymes responsible for the signal transduction processes. Priming procedures may be assessed, for example, by measuring receptor binding ($A_1$ adenosine binding with saturation experiments); a decrease in forskolin-stimulated cAMP; levels of G protein; or release of superoxide ion ($O_2-$), $TXA_2$ (thromboxane), PAF (platelet activating factor), or cytokines (IL-1 or TNFα); and intracellular levels of enzymes responsible for cytokine release (e.g., phospholipase $A_2$). See, e.g., Stewart, *Immunology* 78:152 (1993); Salzer, *J. Clin. Invest.* 85:1135 (1990); Liang *J. Pharmacol. Exp. Ther.* 249:775 (1989). Combinations of hypoxia and priming agents may be used to prime cells for use in the present methods.

Lipids may optionally be conjugated to the priming agent(s) and/or the activating agent(s) by techniques known in the art, in order to increase the bioavailability and/or the affinity of the priming agent or activating agent for the cell. See, e.g. Published U.S. Application No. 20040121406.

Suitable activating agents include agents, methods, and conditions capable of activating antigen-presenting cells. Activating agents include, but are not limited to, $A_1$ adenosine receptor agonists which may or may not be selective and further include, but are not limited to, adenosine; cyclohexyladenosine; various $N^6$-substituted $A_1$ adenosine agonists including but not limited to $N^6$ cyclopentyladenosine, $N^6$R-phenylisopropyladenosine, 2-chloro $N^6$ cyclopentyl adenosine (CCPA), $N^6$ (p-sulfophenyl)alkyl and $N^6$ sulfoalkyl derivatives of adenosine (such as $N^6$-(p-sulfophenyl)adenosine; 1-deaza analogues of adenosine including but not limited to $N^6$ cyclopentyl 1-2-chloro-1-deaza adenosine (1-deaza-2-Cl-CPA); $N^6$ cycloaklyladenosines; $N^6$ bicycloalkyladenosines; ribose modified adenosine receptor analogues including but not limited to 3'-deoxy-R-PIA. See, e.g., Conti, *Naunyn-Schmiedeberg's Arch. Pharmacol.* 348:108 (1993); Trivedi, *J. Med. Chem.* 32:8 (1989); Jacobsen, *J. Med. Chem.* 35:4143 (1992); Thedford, *Expl. Cell. Biol.* 57:53 (1989); Trewyn, *Exp. Pharmacol.* 28:607 (1979); Fleysher, *J. Amer. Chem. Soc.* (August 1968); Fleysher, *J. Amer. Chem. Soc.* (November 1969); cycloalkyladenosines (see e.g., Moos, *J. Med. Chem.* 28:1383 (1985)); analogs of R-PIA, CHA, and CPA (see, e.g., Cristalli, *J. Med. Chem.* 31:1179 (1988)). Van der Wenden, *J. Med. Chem.* 38:4000 (1995); Jacobson, *PJM Med. Res. Rev.* 12:423 (1992); Daly, *J. Med. Chem.* 25:197 (1982).

Activating agents may also include transfection or electroporation with nucleotide sequences encoding the $A_1$ adenosine receptor, administration of cisplatin, dexamethasone, daunorubicin, doxorubicin, mitoxantrone, carbamazepine, allosteric enhancers, and protein kinase inhibitors, adenosine receptor antagonists, preferably $A_2$ adenosine receptor antagonists such as triazoloquinazoline (CGS15943)(Williams *J. Pharmacol. Exp. Ther.* 241:415); pyrazolo[4,3-e]-1,2,4-triazolo[1,5-C]pyrimidine derivatives such as 7-2(phenylethyl)-5-amino-2-(2-furyl)-pyrazolo-[4.3-e]-1,2,4triazolo[1,5-c]pyrimidine (Baraldi, *J. Med. Chem.* 39:1164 (1996); Zocchi *J. Pharmacol. Exp. Ther.* 276: 398 (1996)); 8-(3-chlorostyryl)caffeine (Mathot *J. Pharmacol. Exp. Ther.* 275:245 (1995)); 8-(3-isothiocyanatostyryl) caffeine (Ji, *Drug Dev. Res.* 29:292 (1993)); E-1,3-diakyl-7-methyl-8-(3,4,5-trimethoxy-styryl)xanthines, (E)-1,3-dipropyl-7-methyl-8-(3,4-dimethoxystyryl)xanthine (Shimada, *J. Med. Chem.* 35:2342 (1995); Jackson *J. Pharmacol. Exp. Ther.* 267:1993); 4-(2-[7-amino-2-{2-furyl}{1,2,4}triazolo{2,3-a}{1,3,5}triazin-5-yl-amino]ethyl)phenol (Palmer, *J. Pharmacol. Exp. Ther. Mol. Pharmacol.* 48:970 (1995)); 7-deaza-9phenyladenines (Daly, *Biochem. Pharmacol.* 37:3749 (1988); see also Abstracts from Purines '96, *Drug Dev. Res.*, March 1996 at p. 113 (Vittori et al.), p. 130 (Dionisotti et al.), p. 174 (Suzuki et al.), and p. 179 (Suzuki et al. and Dionisotti et al.), and conditions such as ischemia and reperfusion or ischemia alone.

The priming agent and an activating agent may be formulated together (i.e., encapsulated in) in a liposomal formulation according to techniques known in the art, and then administered concurrently to the subject. See, e.g., U.S. Pat. No. 5,527,528 to Allen et al.; U.S. Pat. No. 5,013,556 to Woodle et al., U.S. Pat. No. 5,882,679 to Needham; and U.S. Pat. No. 5,766,627 to Samkaram et al, the disclosures of which are incorporated herein by reference. The liposomal formulation comprising the priming agent and the activating agent may be formulated in a timed-release formulation such that the priming agent is released prior to the release of the activating agent.

Additional treatments of the cells to be activated may optionally include those which increase the numbers of receptors on the cell (e.g., transfection with plasmid vectors containing cDNA encoding $A_1$ adenosine receptors or electroporation with the cDNA encoding $A_1$ adenosine receptors; treatment with dexamethasone); treatments with desensitizing agents such as: (a) treatment with allosteric enhancers to increase $A_1$ adenosine receptor ligand binding and stabilize $A_1$ adenosine receptor-G protein complexes; (b) treatment with adenosine deaminase to increase $A_1$ adenosine receptor binding; and/or (c) treatment with protein kinase inhibitors to prevent tolerance to $A_1$ adenosine receptor agonists; tyrosine phosphatase inhibitors to enhance LPS-induced TNFα release. G protein-coupled receptor (GPCR)s can undergo desensitization. Prolonged activation of the $A_1$ adenosine receptor with an $A_1$ adenosine receptor agonist can produce reduced sensitivity of the receptor to subsequent activation by agonist challenge, a phenonema known as desensitization. Nie Z, et al, *Mol Pharmacol* 52:456-464, 1997. Both GPCR kinases (GRKs) and arrestins play a role in GPCR desensitization. Kohout T A and Lefkowitz R J, *Mol Pharmacol* 63:9-18, 2003. Moreover, a number of other proteins play a role in desensitization, including hsc 73 (heat shock cognate protein), GTPase activating proteins (GAPs), and regulators of G protein signaling (RGS) proteins. Sarrio S, et al., *Mol Cell Biol* 20:5164-5174, 2000; Clark R B and Rich T C, *Mol Pharmacol* 64:1015-1017, 2003; Sierra D A, et al., *Genomics* 79:177-185, 2002. These proteins can promote desensitization. Activated cells can be treated with one or more antisense oligonucleotides designed to knockout the particular protein or proteins, i.e. GRKs, arrestin, hsc 73, GAP, or RSG, promoting desensitization. An antisense cDNA sequence to one or more of these proteins can be transfected or electroporated into the activated cell to reduce the expression of this protein and decrease its effect on desensitization. Other proteins, such as spinophilin or phosphatases, including alkaline phosphatase, protein phosphatase 1 (PP1), or protein phosphatase 2A (PP2A), can interfere with desensitization of GPCRs. Wang Q, et al., *Science* 304:1940-1944, 2004; Nie Z, et al., *Mol Pharmacol* 52:456-464, 1997. An additional treatment of the activated cell may include transfection or electroporation of the activated cells with cDNA of one or more of these proteins to increase the expression of spinophilin, alkaline phosphatase, PP1 or PP2A to prevent desensitization and thus prolong activation of the activated cell and increase the antigenic response.

Combinations of two or more of the various treatments described above to increase $A_1$ adenosine receptor expression, increase $A_1$ adenosine receptor activation and/or prevent $A_1$ adenosine receptor desensitization may be carried out with respect to the cells to be activated as described herein.

Embodiments of the present invention further relate to a method of increasing a cytotoxic response induced by a cytotoxic cell in which a cytotoxic cell is contacted to an activating agent, the improvement comprising contacting the cytotoxic cell with an $A_1$ adenosine receptor agonist in an amount sufficient to increase the cytotoxic response of the cytotoxic cell.

The cytotoxic response may be biological responses including, but not limited to, tumoricidal activity, tumoristatic activity, phagocytosis, lysis, and production of biological response modifiers. Cytotoxic cells include, but are not limited to, natural killer cells, cytotoxic lymphocytes, lymphokine activated killer cells, macrophages, Kupffer cells, microglia, dendritic cells, antibody secreting cells, and cells secreting other effector molecules. The cytotoxic cells may express at least one $A_1$ adenosine receptor or may be transfected or electroporated with a nucleotide sequence encoding the $A_1$ adenosine receptor, for example, cDNA encoding the human $A_1$ adenosine receptor.

According to other embodiments of the present invention, the method of producing an antigenic response as described above may further comprise priming the cytotoxic cell by contacting the cytotoxic cell with a priming agent in an amount sufficient to prime the cytotoxic cell, and activating the cytotoxic cell by contacting the cytotoxic cell with an activating agent in an amount sufficient to induce the cytotoxic cell to mediate an increase in biological responses including, but not limited to, tumoricidal activity, tumoristatic activity, phagocytosis, lysis, production of biological response modifiers and internal processing of the antigen, internal expression of certain proteins that play a role in the immune response, e.g. major histocompatibility complex (MHC) class I or II or human leukocyte antigen (HLA) protein expression or the expression of other proteins that play a role in signaling pathways that participate in immune responses, e.g. NF-κβ, or human genes for IL-6, IL-1β, TNF-α, and other responses that facilitate an effective immune response.

The measure of cytotoxicity in the methods of the present invention may be an indirect measure of cytotoxicity. Examples of indirect measures of cytotoxicity include a measure of the number of $A_1$ adenosine receptors in the membranes of the antigen-presenting cells, or a measure of the affinity of the antigen-presenting cells for $A_1$ adenosine receptor specific ligands (i.e., a measure of the affinity of the $A_1$ adenosine receptors present in the membranes of the antigen-presenting cells for $A_1$ adenosine receptor specific ligands). The measure of cytotoxicity may also be a functional measure of cytotoxicity as defined herein, in which case the antigen-presenting cells are primed and activated prior to being tested for cytotoxicity.

One indirect method of determining the measure of cytotoxicity of antigen-presenting cells for target cancer cells is evaluating the number of $A_1$ adenosine receptors in the membranes of the antigen-presenting cells according to methods known in the art (e.g., by determining $B_{max}$ using labeled ligand saturation binding techniques, where $B_{max}$ is an expression of the density or number of $A_1$ adenosine receptors present in the membranes of the cells). In general, the higher the number and/or density of $A_1$ adenosine receptors on the antigen-presenting cells, the greater the measure of cytotoxicity of the antigen-presenting cells for target cancer cells.

A second and more preferred indirect method of determining a measure of cytotoxicity of the antigen-presenting cells of the subject is evaluating the affinity of the antigen-presenting cells for $A_1$ adenosine receptor ligands. These measurements of affinity may be carried out using labeled ligand binding measurement techniques known in the art. Ligands may be labeled with radioactive compounds, fluorescent compounds, biotinylated compounds, luminescent compounds, and the like. These methods of evaluating the affinity of the antigen-presenting cells include using saturation binding techniques or competitive binding techniques to determine the affinity of the antigen-presenting cells for $A_1$ adenosine receptor ligands as expressed by $K_d$ (saturation binding experiments) or $K_i$ (competition binding experiments), with the value of $K_i$ and $K_d$ being inversely related to affinity (i.e, the lower the $K_i$ or $K_d$, the higher the affinity). In general, the lower the value of the $K_d$ or $K_i$ of the antigen-presenting cell, the greater the measure of cytotoxicity of the antigen-presenting cell.

Alternatively, or additionally, a measure of cytotoxicity of the antigen-presenting cells may be a functional measure of cytotoxicity. A functional measure of cytotoxicity refers to a measure of at least one indicia of tumoricidal activity (e.g., release of cytotoxins or cytokines by the cells, or the percentage of killed tumor cells by the antigen-presenting cells) exhibited by the antigen-presenting cells. In the practice of the present invention, antigen-presenting cells are primed and activated prior to determining a functional measure of cytotoxicity. See U.S. Pat. Nos. 6,680,052 and 6,159,701 to Neely and Published U.S. Patent Application No. 20030129678 to Neely.

The methods of the present invention may utilize the cytotoxic effects of activated antigen-presenting cells to inhibit the growth of tumors, cancers and other neoplastic tissues.

Embodiments of the present invention relate to methods of enhancing $A_1$ adenosine receptor signaling in an antigen-presenting cell, comprising administering an activating agent to the antigen-presenting cell in an amount sufficient to enhance $A_1$ adenosine receptor signaling in the antigen-presenting cell. Antigen-presenting cells include those described above. Adenosine receptor signaling includes, but is not limited to, cytotoxic responses, tumoricidal responses, production of biological response modifiers and internal processing of the antigen, internal expression of certain proteins that play a role in the immune response, e.g. major histocompatibility complex (MHC) class I or II or human leukocyte antigen (HLA) protein expression or the expression of other proteins that play a role in signaling pathways that participate in immune responses, e.g. NF-κβ, or human genes for IL-6, IL-1β, TNF-α, and other responses that facilitate an effective immune response.

In some embodiments, methods of enhancing $A_1$ adenosine receptor signaling may comprise genetically altering $A_1$ adenosine receptor expression and/or chemically altering $A_1$ adenosine receptor expression. Methods of enhancing $A_1$ adenosine receptor signaling may further comprise correcting an $A_1$ adenosine receptor deficiency in the antigen-presenting cell further comprising administering an agent to the antigen-presenting cell in an amount sufficient to increase the number of $A_1$ adenosine receptors on the antigen-presenting cell plasma membrane. Agents capable of increasing the number of $A_1$ adenosine receptors on the antigen-presenting cell plasma membrane include, but are not limited to, cisplatin, dexamethasone, daunorubicin, doxorubicin, mitoxantrone, carbamazepine, adenosine receptor antagonists, nucleotide sequences encoding the $A_1$ adenosine receptor, for example, cDNA encoding the human $A_1$ adenosine receptor, allosteric enhancers, such as PD 81,723 which increases the affinity and binding of an $A_1$ adenosine receptor ligand for $A_1$ adenosine receptors and coupling of the receptor to the G protein; contacting the cells with divalent cations, including magnesium and calcium; and/or contacting the cells with adenosine deaminase, or immunomodulators or priming agents, such as lymphokines, MDP, MTP, MTP-PE, IFN-γ, PMA, GM-CSF, or fMLP, and protein kinase inhibitors. The number of $A_1$ adenosine receptors may also be increased by subjecting the cells to ischemic conditions. See U.S. Pat. Nos. 5,786,360; 6,117,998; and 6,159,701 to Neely; U.S. Pat. No. 5,320,962 to Stiles et al.; Nie et al., *Mol. Pharmacol.* 53:663 (1998); Gerwins and Fredholm, *Mol. Pharmacol.* 40:149 (1991); Lupica et al. *Synapse* 9:95 (1991); Ren and Stiles, *Mol. Pharmacol.* 55:309 (1999); Biber et al., *Neuropsych. Pharmacol.* 20:271 (1999). The number of $A_1$ adenosine receptors may be increased by treatments described above which prevent receptor desensitization. Moreover, subjects may be administered liposomes comprising nucleotide sequences encoding the $A_1$ adenosine receptor, for example, cDNA for human $A_1$ adenosine receptors, with or without antigens, immunomodulating agents, priming agents, or activating agents, or treatments which prevent desensitization of $A_1$ adenosine receptors as described herein.

Embodiments of the present invention relate to methods of enhancing signaling between an antigen-presenting cell and an effector cell, comprising administering an activating agent in an amount sufficient to enhance signaling between the antigen-presenting cell and the effector cell. Antigen-presenting cells include those described above. Effector cells according to the present invention include, but are not limited to, monocytes, macrophages, lymphocytes, B cells, T cells, natural killer (NK) cells, mast cells, basophils, eosinophils, plasma cells, microglia, Kupffer cells, granulocytes, fibroblasts, and endothelial cells. Activating agents include agents, methods, and conditions capable of activating antigen-presenting cells as described above. The activating agent may be administered in the presence or absence of the antigen.

Embodiments of the invention further relate to compositions and pharmaceutical compositions comprising an antigen. The compositions and pharmaceutical compositions may further comprise an activating agent. The antigen may include those described above. The activating agent may include those described above.

The composition may further comprise an immunomodulator. Non-limiting examples of immunomodulators include lipopolysaccharide (LPS), endotoxin, Lipid A, analogues and derivatives of LPS and Lipid A, muramyl peptides (analogues and derivatives), IFN α, IFN β, IFN γ, GM-CSF, M-CSF, MCP-1, MCP-3, MCP-4, lymphokines, PMA, fMLP, interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-15 (IL-15), interleukin-16 (IL-16), interleukin-17 (IL-17), TNF-α, IL-1ra, MIF, HMGB1, MIP-1α, MIP-1β, MIP-3α, MIP-5/human cc cytokine-2 (HCC2), PAF, prostaglandins, $PGE_2$, leukotrienes, thromboxane, cytokines, chemokines, lymphokines, zymosan, supernatants of tumor cells, enterotoxin, 1,3 beta glucan, peptidoglycan, lipoteichoic acid, RANTES, CD40 ligand (CD 40L), TNF-related activation induced cytokine (TRANCE), TGF-β, Flt 3 ligand (FL), c-kit, C5a, complement, stem cell factor (SCF), hepatocyte growth factor (HGF), macrophage-derived chemokines (MDC), stromal cell derived factor-1α (SDF-1α), and combinations thereof. The composition may further comprise a priming agent. Representative priming agents are described above. The composition may be lyophilized. The composition may further comprise a pharmaceutically acceptable carrier. The pharmaceutically acceptable carrier may be an aqueous carrier or a solid carrier. The carrier is a molecule that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), polymeric particulate carriers, inactive virus particles and the like. Additionally, these carriers may function as additional immunostimulating agents.

The composition may further comprise an adjuvant. Suitable adjuvants include those appropriate to elicit the response of interest or treat the condition of interest and may be used to enhance the effectiveness of the compositions and pharmaceutical compositions described herein. Such adjuvants include, but are not limited to: aluminum salts, such as aluminum hydroxide, aluminum phosphate, aluminum sulfate, etc., oil-in-water emulsion formulations (with or without other specific immunostimulating agents such as muramyl peptides, saponin adjuvants, Complete Freunds Adjuvant (CFA) and Incomplete Freunds Adjuvant (IFA), cytokines, such as interleukins (IL-1, IL-2, etc.), macrophage colony stimulating factor (M-CSF), tumor necrosis factor (TNF), etc., detoxified mutants of a bacterial ADP-ribosylating toxin such as a cholera toxin, a pertussis toxin, or an *E. coli* heat-labile toxin, and other substances that act as immunostimulating agents to enhance the effectiveness of the composition.

The compositions of the present invention described above may be formulated for administration in a pharmaceutical carrier in accordance with known techniques. See, e.g., Remington, *The Science And Practice of Pharmacy* (20th ed. 2000). In the manufacture of a pharmaceutical formulation according to the invention, the composition of the present invention is typically admixed with, inter alia, an acceptable carrier. As noted above, the carrier may be a solid or a liquid, or both, and is preferably formulated with the composition as a unit-dose formulation, for example, a tablet, which may contain from 0.01 or 0.5% to 95% or 99% by weight of the active composition. One or more compositions of the present invention may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces), intraarticular, transdermal, nasal, and inhalational administration, although the most suitable route in any given case will depend on the nature and severity of the condition being treated and on the nature of the particular composition which is being used.

Formulations suitable for oral administration may be presented in discrete units, such as capsules, cachets, lozenges, or tablets, each containing a predetermined amount of the active composition; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active composition and a suitable carrier (which may contain one or more accessory ingredients as noted above). In general, the formulations of the invention are prepared by uniformly and intimately admixing the compositions with a liquid or finely divided solid carrier, or both, and then, if necessary, shaping the resulting mixture. For example, a tablet may be prepared by compressing or molding a powder or granules containing the composition, optionally with one or more accessory ingredients. Compressed tablets may be prepared by compressing, in a suitable machine, the composition in a free-flowing form, such as a powder or granules optionally mixed with a binder, lubricant, inert diluent, and/or surface active/dispersing agent(s). Molded tablets may be made by molding, in a suitable machine, the powdered composition moistened with an inert liquid binder.

Formulations suitable for buccal (sub-lingual) administration include lozenges comprising the active composition in a flavoured base, usually sucrose and acacia or tragacanth; and pastilles comprising the composition in an inert base such as gelatin and glycerin or sucrose and acacia.

Formulations of the present invention suitable for parenteral administration comprise sterile aqueous and non-aqueous injection solutions of the active composition, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

Formulations suitable for rectal administration are preferably presented as unit dose suppositories. These may be prepared by admixing the active composition with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time, injection devices that deliver the formulation intradermally, devices that abrade the stratum corneum to allow uptake of the formulation by the afferent lymphatics in the skin.

Formulations suitable for transdermal administration may also be delivered by iontophoresis (see, for example, *Pharmaceutical Research* 3 (6):318 (1986)) and typically take the form of an optionally buffered aqueous solution of the active composition. Suitable formulations comprise citrate or bis\tris buffer (pH 6) or ethanol/water and contain from 0.1 to 0.2M active ingredient.

Further, the present invention provides liposomal formulations of the compositions disclosed herein and salts thereof. The technology for forming liposomal suspensions is well known in the art. When the composition or salt thereof is an aqueous-soluble salt, using conventional liposome technology, the same may be incorporated into lipid vesicles. In such an instance, due to the water solubility of the composition or salt, the composition or salt will be substantially entrained within the hydrophilic center or core of the liposomes. The lipid layer employed may be of any conventional composition and may either contain cholesterol or may be cholesterol-free. When the composition or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

As discussed above, the liposomal formulations containing the compositions disclosed herein, may be lyophilized to produce a lyophilizate which may be reconstituted with a pharmaceutically acceptable carrier, such as water, to regenerate a liposomal suspension.

The compositions of the present invention may be administered by any means that transports the active agents to the lung, including but not limited to nasal administration, inhalation, and insufflation. The active agents disclosed herein can be administered to the lungs of a patient by any suitable means, but are preferably administered by generating an aerosol comprised of respirable particles, the respirable particles comprised of the active agents, which particles the subject inhales. The respirable particles can be liquid or solid, and they can optionally contain other therapeutic ingredients, including, but not limited to surfactants.

Particles comprised of active agents for practicing the present invention should be administered as a formulation including particles of respirable size: that is, particles of a size sufficiently small to pass through the nose, mouth and larynx upon inhalation and into the bronchi and alveoli of the lungs. In general, respirable particles range from about 0.5 to 10 microns in diameter. Particles of non-respirable size that are included in the aerosol tend to deposit in the throat and be swallowed. Accordingly, the quantity of non-respirable particles in the aerosol is preferably minimized. For nasal administration, a particle size in the range of 10-500 µm is preferred to ensure retention in the nasal cavity. Alternatively, droplets can be given.

Liquid pharmaceutical compositions of active agents for producing an aerosol can be prepared by combining the active agents with a suitable vehicle, such as sterile pyrogen free water. Other therapeutic compounds can optionally be included.

Solid particulate compositions containing respirable dry particles of micronized active agents can be prepared by grinding dry antisense compound with a mortar and pestle, and then passing the micronized composition through a 400 mesh screen to break up or separate out large agglomerates. A solid particulate composition comprising the active agent can optionally contain a dispersant that serves to facilitate the formation of an aerosol. A suitable dispersant is lactose, which can be blended with the active agents in any suitable ratio e.g., a 1 to 1 ratio by weight.

The aerosols of liquid particles comprising the active agents can be produced by any suitable means, such as with a nebulizer. See e.g., U.S. Pat. No. 4,501,729.

Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w, but preferably less than 20% w/w, of the formulation. The carrier is typically water or a dilute aqueous alcoholic solution, preferably made isotonic with body fluids by the addition of, for example, sodium chloride. Optional additives include preservatives if the formulation is not prepared sterile, for example, methyl hydroxybenzoate, antioxidants, flavoring agents, volatile oils, buffering agents and surfactants.

The aerosols of solid particles comprising the active agents can likewise be produced with any solid particulate medicament aerosol generator. Aerosol generators for administering solid particulate medicaments to a subject produce particles, which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders that can be delivered by means of an insufflator or taken into the nasal cavity in the manner of a snuff. In the insufflator, the powder, e.g., a metered dose thereof effective to carry out the treatments described herein, is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant.

The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquefied propellant. During use these devices discharge the formulation through a valve adapted to deliver a metered volume, typically from 10 to 150 μl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation can additionally contain one or more co-solvents, for example, ethanol, surfactants, such as oleic acid or sorbitan trioleate, antioxidants and suitable flavoring agents.

The aerosol, whether formed from solid or liquid particles, can be produced by the aerosol generator at a rate of from about 10 to 150 liters per minute, more preferably from about 30 to 150 liters per minute, and most preferably about 60 liters per minute. Aerosols containing greater amounts of medicament can be administered more rapidly.

Any propellant may be used in carrying out the present invention, including both chlorofluorocarbon-containing propellants and non-chlorofluorocarbon-containing propellants. Thus, fluorocarbon aerosol propellants that may be employed in carrying out the present invention including fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Examples of such propellants include, but are not limited to: $CF_3$—$CHF$—$CF_2H$; $CF_3$—$CH_2$—$CF_2H$; $CF_3$—$CHF$—$CF_3$; $CF_3$—$CH_2$—$CF_3$; $CF_3$—$CHCl$—$CF_2Cl$; $CF_3$—$CHCl$—$CF_3$; cy-$C(CF_2)_3$—$CHCl$; $CF_3$—$CHCl$—$CH_2Cl$; $CF_3$—$CHF$—$CF_2Cl$; $CF_3$—$CHCl$—$CFHCl$; $CF_3$—$CFCl$—$CFHCl$; $CF_3$—$CF_2$—$CF_2H$; $CF_3$—$CF_2$—$CH_3$; $CF_2H$—$CF_2$—$CFH_2$; $CF_3$—$CF_2$—$CFH_2$; $CF_3$—$CF_2$—$CH_2Cl$; $CF_2H$—$CF_2$—$CH_3$; $CF_2H$—$CF_2$—$CH_2Cl$; $CF_3$—$CF_2$—$CF_2$—$CH_3$; $CF_3$—$CF_2$—$CF_2$—$CF_2H$; $CF_3$—$CHF$—$CHF$—$CF_3$; $CF_3$—$O$—$CF_3$; $CF_3$—$O$—$CF_2H$; $CF_2H$—$H$—$O$—$CF_2H$; $CF_2H$—$O$—$CFH_2$; $CF_3$—$O$—$CH_3$; $CF_3$—$O$—$CF_2$—$CF_2H$; $CF_3$—$O$—$CF_2$—$O$—$CF_3$; cy-$CF_2$—$CF_2$—$O$—$CF_2$—; cy-$CHF$—$CF_2$—$O$—$CF_2$—; cy-$CH_2$—$CF_2$—$O$—$CF_2$—; cy-$CF_2$—$O$—$CF_2$—$O$—$CF_2$—; $CF_3$—$O$—$CF_2$—$Br$; $CF_2H$—$O$—$CF_2$—$Br$; and mixtures thereof, where "cy" denotes a cyclic compound in which the end terminal covalent bonds of the structures shown are the same so that the end terminal groups are covalently bonded together. Particularly preferred are hydrofluoroalkanes such as 1,1,1,2-tetrafluoroethane (propellant 134a) and heptafluoropropane (propellant 227). A stabilizer such as a fluoropolymer may optionally be included in formulations of fluorocarbon propellants, such as described in U.S. Pat. No. 5,376,359 to Johnson, the disclosure of which is incorporated herein by reference in its entirety.

The pharmaceutical compositions may further comprise other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

Thus, the present invention provides pharmaceutical formulations comprising compositions in pharmaceutically acceptable carriers for oral, rectal, topical, buccal, parenteral, intramuscular, intradermal, or intravenous, transdermal, intraarticular, nasal, and inhalational administration.

Methods of this invention further comprise administering an effective amount of a composition of the present invention as described above to the subject. The effective amount of the composition, the use of which is in the scope of present invention, will vary somewhat from subject to subject, and will depend upon factors such as the age and condition of the subject, the nature of the disorder to be treated, and the route of delivery. Such dosages can be determined in accordance with routine pharmacological procedures known to those skilled in the art. For example, the compositions of the present invention can be administered to the subject in an amount ranging from a lower limit from about 0.01, 0.05, 0.10, 0.50, 1.0, 5.0, or 10% to an upper limit ranging from about 10, 20, 30, 40, 50, 60, 70, 80, 90, 95, 96, 97, 98, 99, or 100% by weight of the pharmaceutical composition. In some embodiments, the compositions comprise from about 0.05 to about 95% by weight of the pharmaceutical composition. In other embodiments, the compositions comprise from about 0.05 to about 60% by weight of the composition. In still other embodiments, the compositions comprise from about 0.05 to about 10% by weight of the composition.

The therapeutically effective dosage of any specific composition will vary somewhat from composition to composition, patient to patient, and will depend upon the condition of the patient and the route of delivery. As a general proposition, a dosage from about 0.1 to about 50 mg/kg will have therapeutic efficacy, with still higher dosages potentially being employed for oral administration, wherein aerosol administration is usually lower than oral or intravenous administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

In particular embodiments, administration to a subject such as a human, a dosage of from about 0.01, 0.1, or 1 mg/kg up to 50, 100, or 150 mg/kg or more for each active agent can be employed. Depending on the solubility of the particular formulation of active compositions administered, the daily dose can be divided among one or several unit dose administrations. The administration of the active compositions can be carried out therapeutically (i.e., as a rescue treatment) or prophylactically.

Embodiment of the present invention further relate to methods of immunizing a mammal against an antigen comprising administering the compositions and pharmaceutical compositions comprising an antigen as described above. Once obtained, the antigen as described herein may be incorporated into immunogenic or vaccine compositions comprising an activating agent, an adjuvant, and an additional antigen(s). The adjuvant and additional antigen may be administered separately, either simultaneously with, just prior to, or subsequent to, the administration of the composition. The compositions may be used both for treatment and/or prevention of infection.

One or more selected antigens may be administered in a "therapeutically effective amount" such that an immune response may be generated in the individual to which it is administered. The exact amount necessary will vary depending on the subject being treated; the age and general condition of the subject to be treated; the capacity of the subject's immune system to synthesize antibodies and/or mount a cell-mediated immune response; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials. In general, a "therapeutically effective" amount of antigen will be an amount on the order of about 0.1 µg to about 1000 µg, more preferably about 1 µg to about 100 µg.

Once formulated, the compositions of the invention may be administered parenterally, e.g., by injection. The compositions may be injected either subcutaneously, intraperitoneally, intravenously or intramuscularly. Other modes of administration include oral and pulmonary administration, suppositories, mucosal and transdermal applications. Dosage treatment may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also, at least in part, be determined by the need of the subject and be dependent on the judgment of the practitioner. Furthermore, if prevention of disease is desired, the vaccines are generally administered prior to primary infection with the pathogen of interest. If treatment is desired, e.g., the reduction of symptoms or recurrences, the vaccines are generally administered subsequent to primary infection.

Embodiments of the present invention further relate to methods of determining a subject's potential responsiveness to treatment for conditions associated with $A_1$ adenosine receptor deficiency comprising determining $A_1$ adenosine receptor expression, affinity, or function on antigen-presenting cells.

These methods are based upon the inventive premise that the measure of $A_1$ adenosine receptor expression, affinity, or function of the subject's antigen-presenting cells is a reliable predictor of candidacy for treatment for conditions associated with $A_1$ adenosine receptor deficiency comprising methods of diagnosis or treatment and/or administering compositions of the present invention as described herein.

In the inventive method of the present invention, a sample of antigen-presenting cells as described above is first obtained from the subject. Obtaining a sample of antigen-presenting cells from the subject may be carried out by any method known in the art (e.g., isolating cells from blood samples).

After being obtained from the subject, the antigen-presenting cells are then tested for $A_1$ adenosine receptor expression, affinity, or function, the results of the testing providing an indicator of the potential responsiveness to treatment for conditions associated with $A_1$ adenosine receptor deficiency comprising the treatments and administration of compositions described herein.

The antigen-presenting cells may be evaluated for the number of $A_1$ adenosine receptors in the membranes of the antigen-presenting cells according to methods known in the art (e.g., by determining $B_{max}$ using labeled ligand saturation binding techniques, where $B_{max}$ is an expression of the density or number of $A_1$ adenosine receptors present in the membranes of the cells). The affinity of $A_1$ adenosine receptors of the antigen-presenting cells may be evaluated by measuring the affinity of the receptors for $A_1$ adenosine receptor ligands. These measurements of affinity may be carried out using labeled ligand binding measurement techniques known in the art. Ligands may be labeled with radioactive compounds, fluorescent compounds, biotinylated compounds, luminescent compounds, and the like. These methods of evaluating the affinity of the antigen-presenting cells include using saturation binding techniques or competitive binding techniques to determine the affinity of the antigen-presenting cells for $A_1$ adenosine receptor ligands, as expressed by $K_d$ (saturation binding experiments) or $K_i$ (competition binding experiments), with the value of $K_i$ and $K_d$ being inversely related to affinity (i.e, the lower the $K_i$ or $K_d$, the higher the affinity).

Embodiments of the present invention further relate to methods of imaging antigen-presenting cells in a subject, wherein a sample of antigen-presenting cells is taken from a subject and then labeled with a radiolabeled $A_1$ adenosine receptor ligand, radiolabeled $A_1$ adenosine receptor protein, or radiolabeled nucleotide sequence encoding an $A_1$ adenosine receptor protein, preferably the cDNA for the human $A_1$ adenosine receptor directly. The antigen-presenting cells may also be labeled with radiolabeled antigens such as the antigens described above. In some embodiments, the antigen-presenting cell may take up the labeled antigen after the $A_1$ adenosine receptor deficiency has been corrected by the methods described herein including, but not limited to, insertion of a nucleotide sequence encoding $A_1$ adenosine receptors or administration of cisplatin. In other embodiments of the present invention, the imaging technique may include the use of a liposome with the nucleotide sequence encoding $A_1$ adenosine receptors and the labeled antigen. In yet other embodiments, imaging techniques may include the use of a liposome with a labeled priming agent, labeled activating agent, and/or labeled nucleotide sequence encoding $A_1$ adenosine receptors with or without the antigen.

The present invention further relates to methods of imaging antigen-presenting cells in a subject, wherein a sample of antigen-presenting cells is taken from a subject and contacted with a biosensor that binds to or recognizes a specific target on the antigen-presenting cell. As used herein "biosensor" refers to an agent, molecule, compound, and the like that can detect physiological, cellular, or molecular structures and/or processes in the antigen-presenting cells. The biosensor may or may not be radiolabelled. The specific target on the antigen-presenting cell includes, but is not limited to, $A_1$ adenosine receptors. In some embodiments, the specific target is an extracellular domain of an $A_1$ adenosine receptor.

Imaging methods are useful in diagnosing or screening for the presence of a benign or malignant growth, assessing changes in size or extent of a growth, as well as in localizing a growth for treatment, biopsy, or surgical excision. The imaging methods disclosed herein may be employed to image tumors, cancers, infections, tissue rejection (as in the case of transplant rejection or autoimmunity). Subjects are typically humans, but also include veterinary subjects, including but not limited to dogs, cats, horses, cows and other companion and livestock species.

Techniques for preparing and utilizing radioactively labeled adenosine receptor ligands are known in the art. See, e.g., Williams and Jacobson, *Radioligand Binding Assays for Adenosine Receptors*, In: Adenosine and Adenosine Receptors, M. Williams (Ed.), Humana Press, Clifton, N.J. (1990); Patel et al., *Molecular Pharmacology* 33:585 (1988); Williams et al., *Receptor Pharmacology and Function*, Marcel Dekker, New York (1988).

The ability of activated antigen-presenting cells to associate with tumor cells may also be utilized for methods of imaging or diagnosing tumorous or neoplastic growths. In the diagnostic or imaging methods of the present invention, radiolabelled $A_1$ adenosine receptor ligands (preferably selective for $A_1$ adenosine receptors) and/or $A_2$ adenosine receptor antagonist ligands are used to label the cells (such as macrophages). See Palmer, *JPET Mol. Pharmacol.* 48:970, 1995 regarding $A_1$ agonists or $A_2$ antagonists. Where the ligands are $A_1$ adenosine receptor agonists they additionally activate the cells as described above and may serve both imaging and therapeutic purposes. After administration of the radiolabelled activated cells to a subject and after a suitable time has elapsed to allow association of activated cells and tumor cells (which time will vary depending on mode of administration of the labelled activated cells and site of the tumor), detection of the labelling signal is used for imaging or diagnostic (or therapeutic) purposes as are known in the art.

Embodiments of the present invention further relate to diagnostic kits for determining a subject's potential responsiveness to treatment for conditions associated with $A_1$ adenosine receptor deficiency comprising at least one reagent for determining $A_1$ adenosine receptor expression, affinity, or function on antigen-presenting cells of the subject, and printed instructions for assessing the subject's responsiveness to treatment for conditions associated with $A_1$ adenosine receptor deficiency, wherein the at least one reagent and the printed instructions are packaged together in a container.

As used herein, the term "reagent" means any compound, composition or biological agent (i.e., samples, aliquots or "doses" of cells, cDNAs, recombinant DNAs, isolated genes, antibodies, etc.) useful in carrying out any method of the present invention as described herein including, but not limited to, priming agents, activating agents, $A_1$ adenosine receptor ligands (including agonists, antagonists and antibodies to $A_1$ adenosine receptors), antibodies and ligands for cytokines and cytotoxic compounds produced by cells, cDNAs encoding $A_1$ adenosine receptors and compounds useful in transfecting the cDNAs into cells, drugs and other compounds for increasing $A_1$ adenosine receptor expression, drugs and other compounds for increasing affinity of cells for $A_1$ adenosine receptors, drugs and other compounds for stimulating the production of precursor cells for antigen presenting cells, stem cells, antigen presenting cells, dendritic cells, peripheral blood mononuclear cells, monocytes and macrophages and/or the terminal differentiation thereof, buffers and carriers useful in isolating and preparing cells and/or membranes for analysis and treatment, buffers and carriers useful in carrying out saturation and competition binding assays, allosteric enhancers for $A_1$ adenosine receptors, known anti-cancer therapeutic compounds, and radioactive and non-radioactive labeling compounds.

A diagnostic kit of the present invention may include reagents for performing determinations of cytotoxicity of antigen-presenting cells (i.e., reagents for performing tests measuring the number of $A_1$ adenosine receptors in the membranes of antigen-presenting cells, and/or reagents useful in performing tests measuring the affinity of antigen-presenting cells for $A_1$ adenosine receptor ligands as described above. Such kits will include printed instructions for conducting the appropriate tests, and may include instructions for isolating antigen-presenting cells from a subject, instructions for isolating and affixing to a solid support membranes from the antigen-presenting cells for use in the tests, and instructions for conducting the tests themselves. The printed instructions will also include instructions for interpreting the test results for the assessment of interest. The methods may also include use of flow cytometry technology to assay receptor expression through use of $A_1$ adenosine receptor ligands that are conjugated to a fluorophore.

The methods of treatment disclosed herein may be employed with any subject suspected of carrying tumorous growths, cancers, or other neoplastic growths, either benign or malignant ("tumor" or "tumors" as used herein encompasses tumors, cancers, disseminated neoplastic cells and localized neoplastic growths). Examples of such growths include but are not limited to breast cancers; osteosarcomas, angiosarcomas, fibrosarcomas and other sarcomas; leukemias; sinus tumors; ovarian, uretal, bladder, prostate and other genitourinary cancers; colon, esophageal and stomach cancers and other gastrointestinal cancers; lung cancers; lymphomas; myelomas; pancreatic cancers; liver cancers; kidney cancers; endocrine cancers; skin cancers; melanomas; angiomas; and brain or central nervous system (CNS) cancers. In general, the tumor or growth to be treated may be any tumor or cancer, primary or secondary, which is recognized by cytotoxic cells (for example, macrophages) and which induces the tumoricidal effect of the cells upon contact. See, e.g., Alexander and Evans, *Nature New Biology* 232:76 (1971). Additionally, the invention relates to methods of treatment of a condition in which correction of an $A_1$ adenosine receptor deficiency may improve the condition. Methods of the present invention further relate to treating conditions that include, but are not limited to, infectious immunodeficiency disorders, e.g. human immunodeficiency virus (HIV), non-infectious immunodeficiency disorders such as genetic immunodeficiency, immunosuppressive therapies, and neonatal status, CNS disorders, including Alzheimer's Disease, Parkinson's Disease, amyotrophic lateral sclerosis, multiple sclerosis, infectious diseases, autoimmune diseases, such as Myasthenia Gravis, Crohn's Disease, regional enteritis, vasculitis, insulin-dependent diabetes mellitus, tumors, cancer, substance abuse, asthma, contact allergy, transplant rejection, such as organ and tissue grafts, and atherosclerosis.

The methods of producing an antigenic response, including the methods described above for producing an antigenic response and priming and/or activating antigen-presenting cells, may also be employed in combination with known therapies for treatment of the condition of interest.

The following Examples are provided to illustrate the present invention, and should not be construed as limiting thereof.

EXAMPLE 1

Identification of Patients with Prostate Cancer Who will Benefit from $A_1$ Adenosine Receptor-Based Therapeutic Approach: Use of FACS and/or Radioligand Binding to Determine A1 AR Expression on Monocytes, Immature, and Mature Dendritic Cells Antigen Presenting Cells (APCs) are deficient in $A_1$ adenosine receptor expression or affinity in patients with tumors/cancers. This deficiency in $A_1$ adenosine receptor expression and/or affinity in APCs may correlate with tumor burden in cancer patients. More specifically, this study is designed to show that expression of $A_1$ adenosine receptors or $A_1$ adenosine receptor binding affinity on circulating precursors of dendritic cells (DCs) (monocytes), immature or mature dendritic cells of patients with prostate cancer correlates with the patient's tumor burden.

Logistics:
Day 0:
Isolate monocytes
FACS analysis of monocytes and whole blood for $A_1$ adenosine receptor expression
Membrane preparations for radio-ligand binding assays
Culture of cells for production of immature DC
Day 6:
Addition of maturation cocktail to immature DC
Analysis of immature DC by FACS for $A_1$ adenosine receptor expression and immature DC phenotype
Day 7:
Harvest mature DC
Analysis of mature DC by FACS for $A_1$ adenosine expression and mature DC phenotype
Isolation of Monocytes:

Peripheral blood collected from prostate cancer patients are obtained using a protocol approved by the Institutional Review Board. A 100 ml volume of blood is collected in VACUTAINER® tubes containing sodium-EDTA (Becton-Dickinson) and diluted 1:1 (vol/vol) in calcium/magnesium-free Dulbecco's phosphate buffered saline (D-PBS). Peripheral blood mononuclear cells (PBMC) are isolated by a one-step gradient centrifugation using Lymphoprep® (Invitrogen, Life Technologies, Gaithersburg, Md.) followed by platelet removal by centrifugation of PBMC in D-PBS at 400×g and 4° C. The MACS® negative selection kit for isolation of untouched human monocytes are used in accordance with the protocol provided by the manufacturer (Miltenyi Biotec, Auburn Calif.). This technique uses an Fc receptor blocking reagent in combination with biotin-conjugated antibodies directed against cell surface proteins expressed on all PBMC except monocytes to remove all non-monocyte cells from the PBMC sample and leave untouched monocytes. Any unbound antibody is washed from PBMC with a buffer consisting of 0.5% BSA and 2 mM EDTA in D-PBS, after incubation for 10 minutes at 4° C. Streptavidin-coated magnetic beads are added to cells for 15 minutes at 4° C. Unbound beads are removed from the cells by one wash with a large volume of cold buffer. The entire cell suspension passes though a separation column surrounded by a powerful magnet field that traps all non-monocytes. Cold, de-gassed buffer is used to wash untouched monocytes through the column. Cell purity is confirmed by flow cytometry (FACS). The purity of recovered monocytes is routinely greater than 98% using the MACS® system.

Flow Cytometry:

FACS is used as a means of determining $A_1$ adenosine receptor expression in conjunction with labeled antibodies directed against CD14 and CD16 (BD Pharmingen). Alternatively, a commercial polyclonal antibody directed against the human $A_1$ adenosine receptor after purifying the IgG and labeling the antibody with an appropriate fluorophore is used. Neutrophils in whole blood are analyzed via FACS using monoclonal antibodies directed against CD16 and CD56. FACS analysis of A1 AR expression on differentiated dendritic cells is also performed. Monocyte purity is determined by positive expression of CD14, CD11b, CD45 and the absence of CD1a, CD3, CD15, CD19 and CD56 (BD Pharmingen) in comparison to data obtained with isotype controls. Neutrophils are identified with monoclonal antibodies directed against CD16. Immature and matured DC are analyzed for expression of surface proteins characteristic of the mature DC phenotype, CD3−, CD83−, CD86$^{low}$, CD80$^{low}$, CD40−, CD14−, CD19−, CD16−, CD56−, MHC I+, MHC II+. Expression of other surface proteins associated with dendritic cells is also determined, such as CD1, CD1a, CD1c, and CD11c.

Determination of $A_1$ adenosine receptor expression is possible by synthesis of a fluorescently tagged $A_1$ AR ligand also used for saturation binding experiments, BWA844U. Standardized fluorescence quantitation is possible with the BD QUANTIBRITE™ system and CELLQUEST™ software (BD Biosciences).

Cells (5×10$^5$) are resuspended in FACS staining buffer consisting of HBSS (Life Technologies) 1.0% (w/v) BSA (fraction V, Sigma), 0.1% (w/v) NaN$_3$ (Sigma) in a final volume of 45 μl. Non-specific binding is blocked 15 minutes prior to labeling with Fc receptor blocking reagent (Miltenyi Biotec). Antibodies and labeled BWA844U (0.4 nM final concentration) are incubated with cells for 30 minutes on ice, in the dark, using amounts of antibody recommended by the manufacturer (BD Pharmingen). Labeled cells are washed twice and fixed in 100 μl of 1.5% buffered formalin, tubes are covered with aluminum foil and stored at 4° C. until brought to the FACS facility. In the case of whole blood, cells are labeled as described followed by a step to lyse red blood cells with FACS LYSING SOLUTION® (Becton Dickinson). The remaining leukocytes are washed and fixed. During analysis, the appropriate gates will be set through use of forward and side scatter parameters. Background fluorescence is determined by analyzing cells incubated with the appropriate isotype controls as well as unlabeled BWA844U, in tandem with samples. Samples are analyzed in a minimum of duplicates, with a minimum of 20,000 gated events/sample. Analysis of FACS data is performed with the use of FLOJO® Software.

Human Monocyte Culture and Membrane Preparation

Human monocytes will be isolated from prostate cancer patients, washed 3 times with PBS and then suspended in lysis buffer (10 mM Tris HCl pH 7.4, 5 mM EDTA 10 μg/ml soybean trypsin inhibitor, 10 μg/ml benzamidine, 2 μg/ml pepstatin). The cells are homogenized by sonication. The homogenate is centrifuged at 1000×g at 4° C. for 10 minutes. The supernatant is centrifuged at 30000×g for 30 minutes. The pellet is reconstituted in reconstitution buffer (50 mM Tris HCl pH 7.4, 5 mM EDTA, 10 mM $MgCl_2$, 10 μg/ml soybean trypsin inhibitor, 10 μg/ml benzamidine, 2 μg/ml pepstatin). The protein content is determined by Bradford reagent using bovine serum albumin as standard. The aliquots are stored at −80° C. until used.

Radioligand Saturation Binding Experiments

Saturation binding experiments are performed in membrane fractions (~10-20 μg protein) from human monocytes. Binding experiments will be performed with membranes in a total volume of 0.2 ml in 50 mM Tris HCl buffer, adenosine deaminase 0.2 U/ml, pH 7.4 at 37° C. for one hour with the selective A1 AR antagonist radioligand [$^{125}$I] BWA844U (0.4 nM) in the presence of BWA844U (concentrations ranging from 1.25-20 nM). Non-specific binding is determined in the presence of 1 mM theophylline. The incubation is terminated after by filtration over GF/C filters using a cell harvester. The filter bound radioactivity is counted in a gamma counter (CliniGamma, LKB). The data is analyzed by non-linear regression using GraphPad Prism software. The $B_{max}$ and $K_d$ values are calculated from the analyzed data with the use of Graph Pad Prism software. Three experiments are performed for each sample and assayed in duplicate.

Ex Vivo Differentiation of Monocytes into Immature and Mature Dendritic Cells

Monocytes are obtained from the peripheral blood of prostate cancer patients, as previously described. Monocytes are differentiated into immature dendritic cells. The protocol for inducing differentiation of monocytes into dendritic cells is as follows. The media used to culture the purified monocytes is RPMI-1640 with 25 mM Hepes buffer and 2 mM L-glutamine that is supplemented with 20 μg/ml gentamicin (Invitrogen, Life Technologies) 1% heat-inactivated human serum or 1% heat-inactivated autologous plasma and 2 Units/ml of adenosine deaminase.

Monocytes are cultured in 6 well plates (Nunc Nalgene) at a density of 0.5×10$^6$ cells in 3 ml of media/well (Day 0) supplemented with 800 U/ml rhu GM-CSF, 500 U/ml of rhu IL-4 (Immunex, Seattle Wash.) and 2 Units/ml of adenosine deaminase. Cultures are fed every 2 days by adding 0.3 ml media containing supplement amounts of rhu GM-CSF, rhu-IL-4 and adenosine deaminase, at 800 U/ml, 500 U/ml and 2 Units/ml, respectively. Cells are matured for 24 hours using an LPS-free maturation cocktail consisting of IL-1β (10 ng/ml), IL-6 (1000 U/ml), TNF-α (10 ng/ml), and $PGE_2$ (1 ug/ml) (Day 6). On day 7, cells are analyzed via FACS to confirm that DCs have differentiated into a mature phenotype.

Immature and matured DC are analyzed for expression of surface proteins characteristic of the mature DC phenotype, CD3−, CD83−, CD86$^{low}$, CD80$^{low}$, CD40−, CD14−, CD19−, CD16−, CD56−, MHC I+, MHC II+ (BD Pharmingen, San Diego Calif.) and A1 AR expression with labeled BWA844U via QuantiBRITE™. Data for A1 AR expression and radioligand binding is analyzed and correlated with classification of tumor burden for each patient.

Determinants of Tumor Burden:

Patients are classified as having low, moderate, or high tumor burden based on the following classification: Least→greatest 1. Low risk disease at radical prostatectomy (organ-confined, Gleason score≦6) who have had no evidence of biochemical recurrence≧5 years.
2. PSA-recurrent disease after surgery with evidence of biochemical progression within 5 years after definitive treatment.
3. Regional or distant metastatic disease (positive bone scan, CT, or MRI) who have not received cytotoxic chemotherapy.

EXAMPLE 2

A1 AR-Based Approach to Treatment with APCs: Dendritic Cell Vaccine

Logistics:
Day 0:
Isolate monocytes
FACS analysis of monocytes
Lipofection of monocytes with cDNA for human $A_1$ adenosine receptor
Culture of lipofected cells for production of immature DC
Day 6:
Lipofection of immature DC with tumor antigen mRNA
Addition of maturation cocktail to immature DC
Analysis of immature DC by FACS for $A_1$ adenosine receptor expression and immature DC phenotype
Day 7:
Harvest mature DC
Analysis of mature DC by FACS for $A_1$ adenosine receptor expression and mature DC phenotype
Injection into patients Isolation of Monocytes and Transfection of Monocytes with cDNA for the Human $A_1$ Adenosine Receptor Patients undergo a 7-liter leukopheresis procedure to collect leukocytes in sterile saline (200 ml) (Day 0). Peripheral blood mononuclear cells (PBMC) are isolated by a one-step gradient centrifugation using LYMPHOPREP® (Invitrogen, Life Technologies, Gaithersburg, Md.) and washed twice with large volumes of ice-cold D-PBS. Monocytes are isolated and checked for purity as outlined previously. Prior to differentiation into DC, monocytes are transfected with a plasmid preparation coding the cDNA of the human $A_1$ adenosine receptor using non viral means.

Differentiation of Monocytes into Immature Dendritic Cells

Monocytes are cultured in NUNC CELL FACTORIES™ and differentiated into immature DC according to the following protocol (Day 0). Monocytes are cultured and supplemented with 800 U/ml rhu GM-CSF, 500 U/ml of rhu IL-4 (Immunex, Seattle Wash.) and 2 Units/ml of adenosine deaminase. Cultures are fed every 2 days by adding 0.3 ml media containing supplement amounts of rhu GM-CSF, rhu-IL-4 and adenosine deaminase, at 800 U/ml, 500 U/ml and 2 Units/ml, respectively. Cells are analyzed by FACS to determine the percentage of immature, $A_1$ adenosine receptor positive DC.

Protocol for Pulsing Immature DC with Tumor Antigen and Maturation of DC

Immature DC are loaded via lipofection with mRNA coding one or more cancer antigens (Day 6) according to the following method. The method employs a lipid preparation, DMRIE-C (Invitrogen, Life Technologies). DC are washed twice in serum-free medium and resuspended at a concentration of 1-2×10⁶ cells/ml in Opti-MEM (Invitrogen). Diluted tumor antigen mRNA, (250 ul of a 20 ug/ml stock) (Opti-MEM) are combined with diluted DMRIE-C (also diluted in Opti-MEM) to produce a lipid to mRNA ratio of 4:1. This mixture is incubated at room temperature for approximately 15 minutes before being added to the cells. Lipofection proceeds for 2 hours at 37° C. before fresh media is added to the cells, in addition to the previously described LPS-free maturation cocktail consisting of IL-1β (10 ng/ml), IL-6 (1000 U/ml), TNF-α (10 ng/ml), and $PGE_2$ (1 ug/ml). Cells are cultured for another 24 hours then dead cells are removed and viable cells are injected into patients. On day 7 cells will be analyzed via FACS to confirm that DCs have differentiated into a mature phenotype. Cells are analyzed by FACS to determine the percentage of mature, $A_1$ adenosine receptor positive DCs. DCs not used immediately are stored in liquid nitrogen after being suspended in a solution of 50% human AB serum, 40% medium and 10% dimethyl sulphoxide (DMSO).

Protocol for $A_1$ Adenosine Receptor-Based DC Vaccine Therapy for Patients:

Patients receive intravenous injections of DCs pulsed with antigen. Vaccination protocols follow a schedule whereby antigen-pulsed DCs are injected into the patient on each successive round of therapy in PBS. The time between vaccinations may vary, but will generally be in the range of 2 treatments every 2-3 weeks. The numbers of cells/treatment escalates to ensure patients can tolerate the therapy e.g. $10^7$, $5×10^7$ and $10^8$ cells.

Measurement of Antigen-Specific CD8+ Lymphocytes After Vaccination by ELISPOT Assay:

For patients that receive a DC vaccine, the numbers of tumor antigen specific CD8+ cells is also assayed according to ELISPOT assay). Briefly, peripheral blood mononuclear cells are taken from each patient, monocytes ($5×10^4$ cells/well) are added to the wells of MultiScreen-Ha plates (Milipore, Bedford Mass.) that were pre-coated with mouse anti-human IFN-gamma and blocked with media containing serum. The purified monocytes are pulsed with tumor peptide(s) (100 ug/ml) in a final volume of 100 ul for 2 hours at 37° C. Tumor peptide(s) correspond to the mRNA that was initially introduced into the immature DC for the vaccine. After loading monocytes with peptide, purified CD8+ cells ($2×10^5$ cells/well) from the same blood sample are incubated with the monocytes in media. The ELISPOT plate is centrifuged at 150 g for 3 minutes and 100 ul of fresh AIM V media is added to each well. The plates are then incubated under standard tissue culture conditions for 36 hours. The assay is read on an ELISPOT plate reader. Data is compared to wells pulsed with antigen but also incubated with PMA (1 ng/ml) and ionomycin (1 uM) during the 36 hour incubation (positive control). The frequency of antigen specific CD8+ cells is determined at 1 month intervals for a minimum of 3 months.

EXAMPLE 3

Correction of $A_1$ Adenosine Receptor Defect

This study exemplifies the means by which A1 AR defect could be corrected in a more permanent fashion by transfecting DC progenitor cells with cDNA for the human A1 AR followed by injection back into the patient, in order that the body can be repopulated with "corrected DC". Some of these "corrected progenitor cells" may be matured ex vivo into DCs for use as a specific anti-tumor therapy, in conjunction with their corrected stem cell therapy.

Ex Vivo Transfection of DC Precursors (CD 34+) with a Plasmid Containing the cDNA for the Human $A_1$ Adenosine Receptor for Repopulation of the Patient with DC Expressing Greater Amounts of the $A_1$ Adenosine Receptor Protein Patients undergo treatment to mobilize CD34+ cells for purification. These cells are also known as peripheral blood progenitor cells. Patients receive G-CSF (10 ug/kg/day) subcutaneously for four to six days to stimulate production and release of CD34+ progenitor cells from the bone marrow into the peripheral blood. Leukophoresis of the cytokine treated patients would depend on numbers of CD34+ cells in the peripheral blood but routinely occur twice between days 4 and 6.

CD34+ cells are isolated by magnetic bead technology (Miltenyi Biotec) and transfected with plasmid DNA coding the cDNA of the human $A_1$ adenosine receptor. After lipofection cells are cultured overnight in macrophage culture medium containing 10% FBS, 20 μg/ml gentamicin (Invitrogen, Life Technologies) and 2 Units/ml of adenosine deaminase. These cells are expanded in culture using StemSpan™ expansion medium (Stemcell Technologies, Vancouver, Canada) in Nunc Cell Factories™ and supplemented with 100 ng/ml stem cell factor (SCF) (Amgen, Thousand Oaks, Calif.), 50 ng/ml Flt3 ligand (FL) (Peprotech), 20 ng/ml thrombopoietin (Tpo) (Amgen, Thousand Oaks, Calif.), and 10 ng/ml IL-6/soluble IL-6 receptor fusion protein (Hyper-IL-6). These cells are cultured at a density of $10^6$ cells/ml for 10-14 days with growth factors being added every two days. Viable cells are isolated from cultures using the Miltenyi dead cell removal kit and analyzed for A1 AR expression by flow cytometry (FACS). Cells are sorted based on A1 AR expression with only positive cells being isolated and injected into patients intravenously in a similar manner described for the DC vaccine above.

Some $A_1$ adenosine receptor receptor positive cells are cultured further for differentiation into mature DCs, loaded with mRNA coding tumor antigen in vitro according to the protocols outlined above, and used for vaccination (cancer). These transfected and expanded cells will be differentiated into DCs by culture in AIM V medium supplemented with GM-CSF and rh IL-4 (500 Units/ml, R&D Systems) for six days at a density of $0.5×10^6$ cells/ml, with cytokines added every two days. As described previously, lipofection of tumor antigen mRNA precedes DC maturation. Cells can be induced into a mature DC phenotype with the addition of exogenous rh TNF-alpha (10 ng/ml).

Once patients have been reconstituted with DC precursors (CD 34+) progenitor cells, in particular, monocytes with a higher amount of $A_1$ adenosine receptor expression than before (as determined by FACS and RT-PCR), then proceeding with a tumor vaccine is optimal. Such a vaccine may use tumor cells taken from the patient, cultured, irradiated and transfected with a gene encoding a biological response modifier like IL-4, GM-CSF, or a co-stimulatory molecule, before being injected back into the patient (intravenous). The vaccination schedule is similar to those used in the studies described above. Tumor-specific CD8+ lymphocytes are measured using the previously described ELISPOT assay.

EXAMPLE 4

Animal Model of Enhanced Immunity to Hepatitis B Vaccine with an In Vivo $A_1$ Adenosine Receptor-Based Therapeutic Approach Cisplatin is a chemotherapeutic agent that increases the expression of $A_1$ adenosine receptors. An established vaccine is employed to evaluate normal mice which have received pretreatment with several doses of cisplatin or vehicle alone. Mice in each group are sacrificed prior to the vaccine trial and their $A_1$ adenosine receptor expression are determined via FACS and RT-PCR. Ultimately, A1 AR expression is assayed in each animal at the time of sacrifice and related to parameters of immune responsiveness to the vaccine.

BALB/c mice (female, 18-22 g) are used for the study. On days-15 and -7 mice receive varying amounts of the drug cisplatin (Rx protocol) or vehicle (saline). Blood from each mouse (approx 300 ul) is taken by means of a retro-orbital eye bleed after mice have been rendered unconscious with anesthetic (Day-1). Serum from each sample is collected and stored at −80° C. for later analysis. Each animal is vaccinated intraperitoneally with 0.5 ug of HBsAg (H-B-VAX II; MSD, Whitehouse Station, N.J.) (Day 0). One control group receiving vehicle only during cisplatin treatment is injected with HBsAg plus 200 ul of the Ribi Adjuvant System (RAS) (Corixa Corporation, Seattle, Wash.) for use as a positive control. Experimental groups are summarized below; each group is comprised of 15 animals. Each animal receives a second challenge with HBsAg while the positive control group receives HBsAg and Ribi Adjuvant (Day 21).

| Treatment during vaccination trial | Vaccine |
| --- | --- |
| Vehicle alone | HBsAg (0.5 ug ip) |
| Vehicle alone | HBsAg (0.5 ug ip) + 200 ul of Ribi Adjuvant |
| Cisplatin dose 1 mg/kg | HBsAg (0.5 ug ip) |
| Cisplatin dose 2.5 mg/kg | HBsAg (0.5 ug ip) |
| Cisplatin dose 5 mg/kg | HBSAg (0.5 ug ip) |
| Cisplatin dose 5 mg/kg | No Vaccine (Vehicle Alone) |

Detection and Measurement of Antigen Specific Immunoglobulin

On days 7, 21 and 42 mice are bled and the serum is assayed for the production of HBsAg-specific antigen using a commercially available ELISA kit (Biokit USA, Lexington Mass.) according to the manufacturers instructions.

Detection and Measurement of Antigen Specific Cytotoxic T Cells

Spleen and lymph nodes are harvested from all animals and made into single cell suspensions (Day 42). ELISPOT assays are performed to quantify the number of IFN-gamma producing CD8+ lymphocytes according to the manufacturer's instructions (Becton Dickinson). A sample of the recovered cells are analyzed for expression of $A_1$ adenosine receptors via FACS and RT-PCR. The amount of HBsAg specific antibody, numbers of HBsAg specific CD8+ cells and $A_1$ adenosine receptor expression is compared for each animal to determine if increases in $A_1$ adenosine receptor expression correlates with a greater magnitude of both humoral and cellular immunity.

The foregoing is illustrative of the present invention and is not to be construed as limiting thereof. The invention is defined by the following claims, with equivalents of the claims to be included therein.

That which is claimed is:

1. A method of producing an antigenic response in a dendritic cell for injection into a patient, comprising first transfecting, lipofecting, or electroporating CD34+ progenitor cells ex vivo with a nucleotide sequence that encodes an $A_1$ adenosine receptor, then transfecting, lipofecting or electroporating the CD 34+ progenitor cells ex vivo with a mRNA encoding one or more tumor antigens, and lastly differentiating the CD 34+ progenitor cells ex vivo into dendritic cells which are capable of producing an antigenic response of the dendritic cell to the tumor antigen after injection into the patient.

2. The method of claim 1, wherein said dendritic cell is administered to a subject and the antigenic response is an adaptive immune response or an innate immune response.

3. The method of claim 1, wherein the dendritic cell expresses at least one $A_1$ adenosine receptor.

4. The method of claim 1, wherein said transfecting, lipofecting or electroporating step is carried out in vitro.

5. The method of claim 1, wherein the nucleotide sequence is a cDNA encoding a human $A_1$ adenosine receptor.

6. The method of claim 1 further comprising contacting the dendritic cell with an $A_1$ adenosine receptor agonist.

7. The method of claim 1, wherein the antigenic response is an adaptive immune response or an innate immune response.

8. The method of claim 1, wherein said antigenic response is an immune response.

9. The method of claim 8 wherein the immune response is an increase in responsiveness to the tumor antigen.

10. The method of claim 8, wherein the dendritic cell is administered to a subject and the immune response is the production of higher antibody titres, increase in antibody affinity or generation of cytotoxic cells.

11. The method of claim 8, wherein the immune response is the generation of cytotoxic cells.

12. The method of claim 1, further comprising the step of: priming the antigen-presenting cell by contacting the antigen-presenting cell with a priming agent in an amount sufficient to prime the antigen-presenting cell, wherein the priming agent is phorbol myristoyl acetate (PMA).

13. The method of claim 12 further comprising contacting the dendritic cell with an $A_1$ adenosine receptor agonist.

14. A method of enhancing $A_1$ adenosine receptor signaling in a dendritic cell, comprising first transfecting, lipofecting or electroporating CD34+ progenitor cells ex vivo with a nucleotide sequence that encodes an $A_1$ adenosine receptor, then transfecting, lipofecting or electroporating the CD 34+ progenitor cells ex vivo with a mRNA encoding one or more tumor antigens, and lastly differentiating the CD 34+ progenitor cells ex vivo into dendritic cells which are capable of enhancing $A_1$ adenosine receptor signaling in the dendritic cell.

15. The method of claim 14, wherein enhancing $A_1$ adenosine receptor signaling comprises correcting an $A_1$ adenosine receptor deficiency in the dendritic cell.

16. The method of claim 14, wherein the nucleotide sequence is a cDNA encoding a human $A_1$ adenosine receptor.

* * * * *

UNITED STATES PATENT AND TRADEMARK OFFICE
CERTIFICATE OF CORRECTION

PATENT NO.         : 8,247,231 B2
APPLICATION NO.    : 10/903933
DATED              : August 21, 2012
INVENTOR(S)        : Connie N. Wilson and Paul Borron It is certified that error appears in the above-identified patent and that said Letters Patent is hereby corrected as shown below:

The original request for the Certificate of Correction was misstated previously and is correctly stated here:

Page 16, column 30, lines 39-43, Claim 12 (Original claim 15) shown as:
12. The method of Claim 1, further comprising the step of: priming the antigen-presenting cell by contacting the antigen-presenting cell with a priming agent in an amount sufficient to prime the antigen-presenting cell, wherein the priming agent is phorbol myristoyl acetate (PMA).

Page 16, column 30, lines 39-43, Claim 12 (Original claim 15) should read:
12. The method of Claim 1, further comprising the step of: priming the dendritic cell by contacting the dendritic cell with a priming agent in an amount sufficient to prime the dendritic cell, wherein the priming agent is phorbol myristoyl acetate (PMA).

Signed and Sealed this
Eighth Day of January, 2013

David J. Kappos
*Director of the United States Patent and Trademark Office*